United States Patent [19]

Kordes

[11] Plant 5,012

[45] Mar. 29, 1983

[54] ROSE PLANT—727

[75] Inventor: Reimer Kordes, Sparrieshoop, Fed. Rep. of Germany

[73] Assignee: Jackson & Perkins Company, Medford, Oreg.

[21] Appl. No.: 299,167

[22] Filed: Sep. 3, 1981

[51] Int. Cl.[3] ..... A01H 5/00

[52] U.S. Cl. ..... Plt./17

[58] Field of Search ..... Plt./17

*Primary Examiner*—Robert E. Bagwill

*Attorney, Agent, or Firm*—Klarquist, Sparkman, Campbell, Leigh, Whinston & Dellett

[57] ABSTRACT

A hybrid tea rose variety having a bushy, well-branched plant; lengthy stems produced in greenhouse conditions; flowers similar to, but larger than, variety Mercedes; orange-red color; and little fragrance.

1 Drawing Figure

This present invention relates to a new and distinct variety of rose plant of the hybrid tea class which was originated by me by crossing the variety Mercedes, U.S. Plant Pat. No. 3,724, with an unnamed variety.

The primary objective of this breeding was to produce a new rose variety combining the color and form of the variety Mercedes with longer stems and larger blooms of pollen parent. This objective was substantially achieved along with other desirable improvements as evidenced by the following unique combination of characteristics which are outstanding in the new variety and which distinguish it from its parents as well as from all other varieties of which I am aware:

1. A bushy, well branched plant, producing stems in greenhouse conditions of 20 to 24 inches, occasionally longer.
2. Flowers similar to flowers of the variety Mercedes in color and form, but generally larger.
3. Color near Orange-Red, near 34B and C.
4. Little fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Mercedes, U.S. Plant Pat. No. 3,724.

*Pollen parent.*—Unnamed variety.

Classification:

*Botanical.*—Rosa hybrid.

*Commercial.*—Hybrid tea.

FLOWER

Observations made from specimens grown in a greenhouse at Irvine, Calif. in January.

Blooming habit: Continuous.

Bud:

*Size.*—1⅛" to 1¼" when petals start to unfurl.

*Form.*—Blunt top, ovoid.

*Color.*—When sepals first divide, Near Red 41B and 41C; when half blown, upper side of petals Near-Orange Red 31A, lower side of petals Near Orange-Red 31B.

*Sepals.*—Color: Outer surface Near Green 138B; three appendaged sepals lightly appendaged.

*Receptacle.*—Color: Green 138B. Shape: Funnel. Size: Large. Surface: Smooth.

*Peduncle.*—Length: Medium. Surface: Slightly prickly and glandular. Color: Light green. Strength: Stiff, erect, heavy.

*Opening.*—Outer petals curl outward.

Bloom:

*Size.*—Large. Average open size 4" to 4½".

*Borne.*—Singly.

*Stems.*—Long, strong.

*Form.*—When first open, high centered. Permanence: Flattens, outer petals curl back.

*Petalage.*—Number of petals under normal conditions: 40.

*Color.*—Center of flower: Upper side of petals Near Orange-Red 34B. Reverse side of petals Orange-Red 34C. Base of petals at point of attachment Near White. General tonality from a distance: Orange-Red 34C.

*Variegations.*—Often outer petals contain green, vegetative-like streaks.

*Discoloration.*—General tonality at end of first day, no change; third day, very little change.

*Fragrance.*—Slight.

Petals:

*Texture.*—Thick.

*Shape.*—Oval.

*Form.*—Tips slightly recurved, edges slightly quilled.

*Arrangement.*—Imbricated. Petaloids in center, few.

*Persistence.*—Drop off cleanly.

*Lastingness.*—On the plant, very long. As cut flower, very long.

Reproductive parts:

*Anthers.*—Small. Color, yellow. Arrangement, regular around styles.

*Filaments.*—Color: Yellow.

*Pollen.*—Lemon yellow.

*Styles.*—Color: Whitish.
*Stigmas.*—Color: Yellow.

PLANT

Form: Bush.
Growth: Very vigorous, upright.
Foliage:
*Number of leaflets on normal mid-stem leaves.*—5, occasionally 7.
*Size.*—Medium.
*Quantity.*—Normal.
*Color.*—New foliage: Light Green overlaid with Greyed Purple 187C. Old foliage: Dark Green, near 131A.
Leaflets:
*Shape.*—Oval.
*Texture.*—Leathery.
*Edge.*—Serrated.
*Serration.*—Single, large.
*Petiole.*—Rachis: Color, reddish. Underside: Prickles.
*Stipules.*—Long, bearded.

*Disease resistance.*—Normally resistant to mildew under normal growing conditions at Irvine, Calif.
Wood:
*New wood.*—Color: Light green. Bark: Smooth.
*Old wood.*—Color: Green. Bark: Smooth.
Prickles:
*Quantity.*—On main stalks from base, many. On laterals from stalk, ordinary.
*Form.*—Long base, long, hooked downward.
*Color when young.*—Brown.
*Position.*—Irregular.
Small prickles:
*Quantity.*—On main stalks, many. On laterals, few.
*Color.*—Brown.

I claim:

1. A new and distinct variety of rose plant of the hybrid tea class, substantially as herein shown and described, characterized particularly as to novelty by the unique combination of its vigorous bushy plant, producing long stemmed blooms of orange-red color, similar to those of variety Mercedes, and having little fragrance.

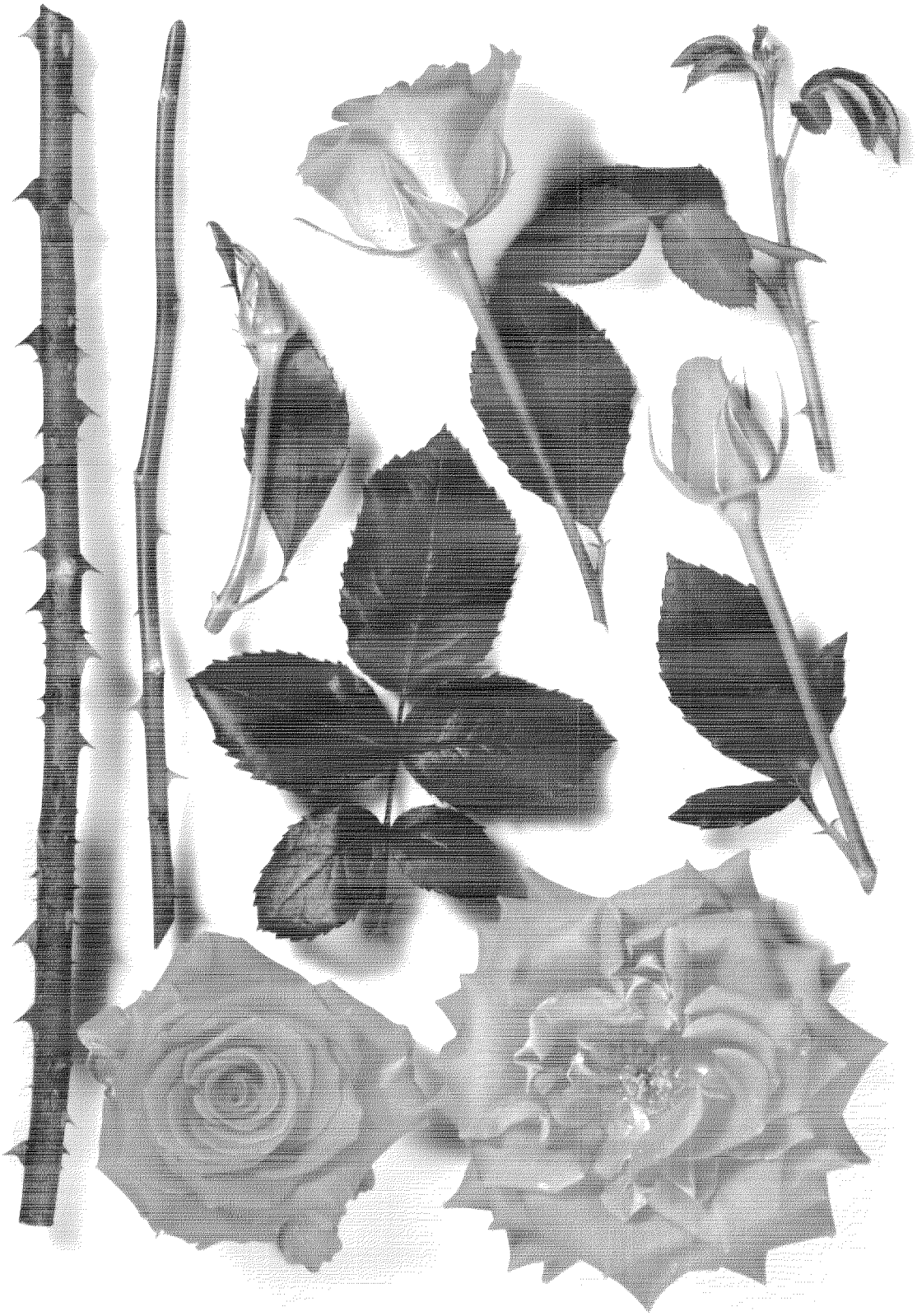

* * * * *